US012127794B2

(12) United States Patent
Oubel et al.

(10) Patent No.: US 12,127,794 B2
(45) Date of Patent: Oct. 29, 2024

(54) METHOD FOR PLANNING TISSUE ABLATION BASED ON DEEP LEARNING

(71) Applicant: Quantum Surgical, Montpellier (FR)

(72) Inventors: Estanislao Oubel, Montpellier (FR); Lucien Blondel, Montpellier (FR); Fernand Badano, Lyons (FR); Bertin Nahum, Castelnau-le-Lez (FR)

(73) Assignee: QUANTUM SURGICAL, Montpellier (FR)

( * ) Notice: Subject to any disclaimer, the term of this patent is extended or adjusted under 35 U.S.C. 154(b) by 161 days.

(21) Appl. No.: 17/597,042

(22) PCT Filed: Jun. 25, 2020

(86) PCT No.: PCT/EP2020/067777
§ 371 (c)(1),
(2) Date: Dec. 23, 2021

(87) PCT Pub. No.: WO2020/260433
PCT Pub. Date: Dec. 30, 2020

(65) Prior Publication Data
US 2022/0233242 A1    Jul. 28, 2022

(30) Foreign Application Priority Data
Jun. 27, 2019  (FR) ...................... 1907000

(51) Int. Cl.
*A61B 18/00*  (2006.01)
*A61B 18/02*  (2006.01)
(Continued)

(52) U.S. Cl.
CPC .............. *A61B 34/10* (2016.02); *A61B 18/02* (2013.01); *A61B 18/04* (2013.01);
(Continued)

(58) Field of Classification Search
CPC ......... A61B 34/10; A61B 18/02; A61B 18/04; A61B 18/1815; A61B 18/20; A61B 34/20;
(Continued)

(56) References Cited

U.S. PATENT DOCUMENTS

| 10,603,511 B2 * | 3/2020 | Bzdusek ................ G16H 20/40 |
| 2007/0053491 A1 * | 3/2007 | Schildkraut ............... G06T 7/12 |
| | | 378/65 |

(Continued)

FOREIGN PATENT DOCUMENTS

| CN | 101859341 A | 10/2010 |
| CN | 105636541 A | 6/2016 |

(Continued)

OTHER PUBLICATIONS

Jarrett et al., "Applications and limitations of machine learning in radiation oncology", Jun. 3, 2019 (Jun. 3, 2019). pp. 1-18, Retrieved from the Internet: www.ncbi.nlm.nih.gov/pmc/articles/PMC6724618/ [retrieved on Apr. 17, 2020].

(Continued)

*Primary Examiner* — Adil Partap S Virk
(74) *Attorney, Agent, or Firm* — ArentFox Schiff LLP

(57) ABSTRACT

The invention relates to a method and device for planning a surgical procedure aiming to ablate a tissue in an anatomical area of interest of a patient. On the basis of a preoperative image of the anatomical area of interest and of a set of planning parameters (P), a simulated image is generated by a neural network that has been previously trained using learning elements corresponding, respectively, to a similar surgical procedure for ablating a tissue in an anatomical area of interest for another patient. Each learning element comprises a preoperative image of the anatomical area of interest of a patient, planning parameters (P) used for the surgical (Continued)

procedure on this patient, and a postoperative image of the anatomical area of interest of this patient after the surgical procedure. An estimated ablation region may be segmented in the simulated image in order to be compared with a segmented region to be treated in the preoperative image.

15 Claims, 6 Drawing Sheets

(51) Int. Cl.
| | |
|---|---|
| A61B 18/04 | (2006.01) |
| A61B 18/18 | (2006.01) |
| A61B 18/20 | (2006.01) |
| A61B 34/10 | (2016.01) |
| G06N 3/045 | (2023.01) |
| G06N 3/08 | (2023.01) |
| G16H 20/40 | (2018.01) |
| G16H 30/40 | (2018.01) |
| G16H 50/50 | (2018.01) |
| G16H 50/70 | (2018.01) |

(52) U.S. Cl.
CPC .......... *A61B 18/1815* (2013.01); *A61B 18/20* (2013.01); *G06N 3/045* (2023.01); *G06N 3/08* (2013.01); *G16H 20/40* (2018.01); *G16H 30/40* (2018.01); *G16H 50/50* (2018.01); *G16H 50/70* (2018.01); *A61B 2018/00577* (2013.01); *A61B 2034/104* (2016.02); *A61B 2034/105* (2016.02); *A61B 2034/107* (2016.02); *A61B 2034/108* (2016.02)

(58) Field of Classification Search
CPC .... A61B 2018/00577; A61B 2034/104; A61B 2034/105; A61B 2034/107; A61B 2034/108; A61B 2034/2051; A61B 2034/2063; A61B 2034/2065; A61B 18/00; G06N 3/045; G06N 3/08; G16H 20/40; G16H 30/40; G16H 50/50; G16H 50/70

See application file for complete search history.

(56) References Cited

U.S. PATENT DOCUMENTS

| | | | | |
|---|---|---|---|---|
| 2007/0092864 A1* | 4/2007 | Reinhardt | ............... | G06T 7/11 600/300 |
| 2008/0287783 A1* | 11/2008 | Anderson | ............ | A61B 8/5238 600/429 |
| 2009/0238434 A1* | 9/2009 | Feke | ................ | G06T 1/0007 382/132 |
| 2010/0063496 A1* | 3/2010 | Trovato | ................ | A61B 90/36 606/34 |
| 2011/0015628 A1* | 1/2011 | Dalal | ................ | A61B 18/1477 606/34 |
| 2013/0116681 A1 | 5/2013 | Zhang | | |
| 2015/0093007 A1* | 4/2015 | Beaumont | ............. | G16H 30/40 382/131 |
| 2018/0028261 A1* | 2/2018 | Chen | .................. | A61B 8/085 |
| 2019/0159823 A1 | 5/2019 | Yang et al. | | |
| 2021/0137384 A1* | 5/2021 | Robinson | ............. | A61B 5/0036 |

FOREIGN PATENT DOCUMENTS

| | | |
|---|---|---|
| CN | 107049475 A | 8/2017 |
| CN | 107441637 A | 12/2017 |
| CN | 107545137 A | 1/2018 |
| CN | 109077804 A | 12/2018 |
| CN | 109166613 A | 1/2019 |
| CN | 109843377 A | 6/2019 |
| JP | 2017514637 A | 6/2017 |
| WO | 2016088075 A1 | 6/2016 |

OTHER PUBLICATIONS

Jalalimanesh et al., "Simulation-based optimization of radiotherapy: Agent-based modeling and reinforcement learning", Mathematics and Computers in Simulation, NL, vol. 133, Mar. 1, 2017 (Mar. 1, 2017), pp. 235-248.

Thiam, "Dosimetrie en radiotherapie et curietherapie par simulation Monte-Carlo GATE surgrille informatique", Oct. 12, 2007 (Oct. 12, 2007), Retrieved from the Internet: http://pdfs.semanticscholar.org/3471/98896cd09201e24fd5ed2ba186976a5ff072.pdf?ga=2.259339530.1650296316.1598017069-2143549959.1598017069 [retrieved on Aug. 21, 2020].

International Search Report and Written Opinion dated, Sep. 1, 2020, issued in PCT International Application No. PCT/EP2020/067777.

Jeong et al., "The Role of Radiotherapy in the Treatment of Gastric Mucosa-Associated Lymphoid Tissue. Lymphoma Ju-Young Song Chonnam National University", Cancer Research and Treatment, Jan. 31, 2014 (Jan. 31, 2014).

\* cited by examiner

METHOD FOR PLANNING TISSUE ABLATION BASED ON DEEP LEARNING

CROSS-REFERENCE TO RELATED APPLICATIONS

This application is a National Phase of PCT/EP2020/067777, filed on Jun. 25, 2020, which claims priority to French Patent Application No. FR1907000, filed on Jun. 27, 2019, the disclosures of which are hereby incorporated by reference in their entireties.

FIELD OF THE INVENTION

The present invention belongs to the field of mini-invasive tissue ablation medical procedures. In particular, the invention relates to a method and a device for planning a surgical procedure aiming to ablate a tissue in an anatomical area of interest of a patient.

STATE OF THE ART

To prepare a surgical procedure aiming to ablate a tissue (for example a tumor) in an anatomical area of interest of a patient (for example a lung, a kidney or the liver), a practitioner generally plans for the procedure based on a preoperative image. The preoperative image is, for example, obtained by computerized tomography (or CT-scan), by magnetic resonance imaging (MRI), by ultrasound, by positron emission tomography (PET or PET-scan), etc.

The ablation of the tissue can be performed by various methods: by heat or by cold (radiofrequencies, microwaves, cryotherapy), by laser, by electroporation, by focused ultrasound, etc. Also, various types of medical instruments can be used for the ablation treatment (needle, probe, electrode, etc.).

Conventionally, the planning of a surgical procedure aiming to ablate a tissue in an anatomical area of interest of a patient who for example might have a hepatocellular carcinoma or metastases with a particular medical instrument is based on medical instrument data supplied by the manufacturer of said instrument. For example, for a particular ablation needle suitable for destroying the cells of a tissue from an electrical current circulating in the needle, the manufacture of said needle indicates the dimensions, the form and the position with respect to the end of the needle of the ablation zone likely to be obtained for different treatment parameters such as an electrical power applied, a treatment duration, etc.

However, for a particular set of treatment parameters, the ablation zone indicated by the manufacturer is determined from ex vivo measurements, and it does not always correspond to the ablation zone actually obtained in vivo on a patient with the same treatment parameters.

Certain tissue ablation planning methods are based also on modelings to simulate the result of the surgical procedure. For example, based on the nature of the tissue to be ablated (for example based on the phenotype of a tumor), characteristics such as heat diffusion or electrical conductivity within the tissue can be estimated to simulate the result of the ablation. According to another example, the result of the ablation is estimated by taking account of a cooling effect by blood vessels situated in or in proximity to the tissue to be ablated. Corrections can then be applied to the medical instrument manufacturer data based on the model envisaged.

Such methods do however remain often imprecise because these modelings are limited by the choice of certain factors considered to be important by the person skilled in the art. Furthermore, these methods sometimes require the insertion of a medical tool into the anatomical area of interest of the patient to measure certain characteristics of the tissue (for example the insertion of electrodes to measure the electrical impedance of the tissue).

Also, in the case where the surgical procedure requires several treatments, simultaneously or in succession, with the possible use of several different needles, conventional planning methods consider that the ablation region obtained corresponds to the union of the ablation zones estimated respectively for each needle and each treatment. Now, that is not always the case. The fact of applying several treatments can in fact have an impact on the ablation zone obtained for each treatment. Also, these conventional methods generally consider that the ablation zone obtained for a particular needle with a particular set of treatment parameters will always be identical. There again, that is only an imperfect estimation. The ablation zone obtained depends in fact not only on the needle and on the treatment parameters used but also on the particular characteristics of the anatomy of the patient.

The patent application US 2018/0028261 A1 discloses a method for assisting a practitioner in the determination of an ablation region of a tumor. The method comprises a step of acquisition of a preoperative medical image of the anatomy of a patient in which the tumor must be ablated. The tumor is segmented on the preoperative image, and the image is analyzed by a machine learning algorithm to determine an ablation region on the preoperative medical image.

The document considers that to ablate all of a tumor is generally wrong and that it is therefore best to appropriately choose the parts of the tumor to be ablated. The most vascularized parts of the tumor are the most risky parts that should be ablated as a priority. The method disclosed in the patent application US 2018/0028261 A1 proposes mapping the blood vessels present in the tumor to identify the parts of the tumor that should be ablated as a priority. The objective of the method described in that document is to optimize the positioning of several identical ablation zones to partially but optimally "cover" the tumor.

However, that document does not address the issue whereby an estimated ablation zone for a particular set of treatment parameters may be different from the ablation zone actually obtained because of certain parameters inherent to the patient. On the contrary, in the method disclosed by that document, an estimated ablation zone for a set of given treatment parameters with a given ablation instrument is always the same. In the method disclosed by that document, several identical ablation instruments are used, and the estimated ablation region corresponds to the union of the ablation zones estimated respectively for each instrument.

There is therefore still a need for a method for planning an ablation of a tissue in an anatomical area of interest of a patient which makes it possible to easily and accurately estimate the ablation region which will actually be obtained for a particular set of treatment parameters.

SUMMARY OF THE INVENTION

The objective of the present invention is to remedy all or some of the drawbacks of the prior art, notably those set out above, by proposing a solution that makes it possible to accurately estimate an ablation region which will be obtained during a specific procedure on a particular patient.

To this end, and according to a first aspect, the present invention proposes a method for planning a surgical procedure aiming to ablate a tissue in an anatomical area of interest of a patient. The method comprises the following steps:
- an acquisition of a preoperative image of the anatomical area of interest,
- a determination of a set of planning parameters,
- a generation of a simulated image in which an estimated ablation region is represented, said simulated image being generated based on the preoperative image, the planning parameters and a neural network, said neural network having been trained previously with a plurality of learning elements, each learning element corresponding respectively to a similar tissue ablation surgical procedure in an anatomical area of interest for another patient, each learning element comprising a preoperative image of the anatomical area of interest of said other patient, planning parameters used for said surgical procedure on that other patient, and a postoperative image of the anatomical area of interest of that other patient after the surgical procedure, said simulated image making it possible to observe the result likely to be obtained after the surgical procedure.

A learning element of the neural network thus corresponds to a triplet of data formed by the preoperative image, a set of planning parameters and a postoperative image.

The preoperative and postoperative images are for example obtained by a medical imaging device, for example by computerized tomography, by magnetic resonance, by ultrasound, by three-dimensional rotating angiography, by positon emission tomography, etc. A preoperative image is obtained before the ablation surgical procedure is performed. A postoperative image is obtained after the ablation surgical procedure has been performed.

During the learning phase of the neural network, for each learning element, the neural network learns what is the ablation region actually obtained on the postoperative image for a particular preoperative image and with particular planning parameters. The neural network is thus trained to estimate accurately, from a particular preoperative image and for a particular set of planning parameters, what will be the ablation region actually obtained. The ablation region thus estimated is represented on a computer-generated image.

Such provisions make it possible to take account of all of the information contained in the medical image of the anatomical area of interest of the patient to make the prediction of the ablation region. Thus, in the method according to the invention, and contrary to the conventional methods of the prior art, the prediction of the ablation region is specific to a given patient.

Some surgical procedures associated with certain learning elements of the neural network may have required the use of several medical instruments. The neural network is thus capable of learning, by analyzing the associated postoperative images, the impact, on the result obtained, of the fact that several medical instruments are used during a procedure.

In the method according to the invention, no in vivo measurement of the patient is necessary. It is therefore possible to perform the planning upstream of the surgical procedure. That makes it possible to offer the practitioner more time to prepare the procedure.

In particular implementations, the invention can further comprise one or more of the following features, taken alone or according to all technically possible combinations.

In particular implementations, the method comprises a segmentation of an estimated ablation region represented on the simulated image. The segmenting of an estimated ablation region makes it possible to define the dimensions of said ablation region, for example to compare it with a region to be treated that is identified on the preoperative image.

In particular implementations, the method further comprises a determination of a tissue response to the ablation procedure by associating, with each voxel of the estimated ablation region represented on the simulated image, a value, called "X-ray density value", representative of an X-ray density of a tissue corresponding to said voxel. In preferred implementations for which a tissue response is determined, the preoperative image is obtained by computerized tomography (or CT-scan).

The word "voxel" is formed by the merging and the contraction of the words "volume" and "element". A voxel is the equivalent of a pixel on a three-dimensional digital image. In the case where the images used are in two dimensions, the term voxel can be replaced by the term pixel. A voxel makes it possible to store colorimetric information and, if necessary, other information for a basic portion of a digital image.

"X-ray density" is understood to mean the relative inability of electromagnetic radiations, in particular X-rays, to pass through a particular material. The more a voxel of the ablation region is associated with a low X-ray density value, the more the part of the ablation region corresponding to said voxel has been destroyed. "Tissue response to the ablation procedure" is thus understood to mean a representation of the proportion with which each part of the tissue to be treated has been ablated. For example, the voxels of the ablation region for which the X-ray density value is above a predetermined first threshold correspond to the parts of the tissue to be treated that have been at least 50% destroyed (which corresponds to a relatively low tissue response to the treatment). According to another example, the voxels of the ablation region for which the X-ray density value is below a predetermined second threshold correspond to the parts of the tissue to be treated that have been more than 90% destroyed (which corresponds to a relatively strong tissue response to the treatment). It is thus possible to map, based on the simulated image, the estimated response of the tissue to the treatment.

In particular implementations, the segmentation of the estimated ablation region is performed such that each voxel of said ablation region is associated with an X-ray density value above a predetermined threshold.

In particular implementations, the method further comprises a check that, for each point of the outline of the estimated ablation region, a gradient of the X-ray density values at this point in a direction normal to said outline is above a predetermined threshold.

Such provisions make it possible in particular to check whether the outline of the ablation region is sharp. The outline of the ablation region marks the limit between the treated region and the untreated tissue. The sharpness of this outline is representative of the quality of the ablation.

In particular implementations, the method further comprises a segmentation on the preoperative image of a region to be treated corresponding to the tissue that the surgical procedure aims to ablate, and a comparison of the estimated ablation region represented on the simulated image with the region to be treated represented on the preoperative image.

Such provisions notably make it possible to check whether the estimated ablation region covers the region to be treated with sufficient margins without the margins being too great. That notably makes it possible to check whether the planning parameters envisaged are valid.

In particular implementations, the method further comprises a check on a validity condition which is satisfied if the outline of the estimated ablation region completely encompasses the outline of the region to be treated, and if, for each point of the outline of the estimated ablation region, the minimum distance between this point and the outline of the region to be treated lies within a predetermined range of values.

In particular implementations, when the check on the validity condition is negative (that is to say if the validity condition is not satisfied), the method comprises a determination of a new set of planning parameters for which the estimated ablation region satisfies the validity condition.

In particular implementations, the method further comprises a step of determination of several new sets of planning parameters for which the validity condition is satisfied, and a step of identification, from among the new sets of planning parameters, of an optimal set of planning parameters for which the estimated ablation region exhibits minimal dimensions.

In particular implementations, the anatomical area of interest is the liver.

In particular implementations, the tissue to be ablated is a tumor.

In particular implementations, the planning parameters comprise one or more elements from among the following elements:
a type of pathology,
a type of treatment,
a type of medical instrument to be used for the treatment,
a position and/or an orientation of the medical instrument to be used for the treatment,
treatment parameters specific to the medical instrument,
a number of treatments to be performed during the surgical procedure.

According to a second aspect, the present invention relates to a computer program product comprising a set of program code instructions which, when they are executed by one or more processors, configure the processor or processors to generate, using a neural network, a simulated image, on which there is represented an estimated ablation region from, on the one hand, a preoperative image of an anatomical area of interest of a patient comprising a tissue to be ablated, and, on the other hand, planning parameters. The neural network is adapted to be previously trained with a plurality of learning elements, each learning element corresponding respectively to a similar tissue ablation surgical procedure in an anatomical area of interest for another patient, each learning element comprising a preoperative image of the anatomical area of interest of said other patient, planning parameters used for said surgical procedure on that other patient, and a postoperative image of the anatomical area of interest of that other patient after the surgical procedure.

According to a third aspect, the present invention relates to a device for planning a surgical procedure aiming to ablate a tissue in an anatomical area of interest of a patient. The device comprises a control unit configured to generate a simulated image based on a preoperative image of said anatomical area of interest, a set of planning parameters and a neural network. The neural network is adapted to be previously trained with a plurality of learning elements, each learning element being associated respectively with a similar tissue ablation surgical procedure in an anatomical area of interest for another patient. Each learning element comprises a preoperative image of the anatomical area of interest of said other patient, planning parameters used for said surgical procedure on that other patient, and a postoperative image of the anatomical area of interest of that other patient after the surgical procedure.

In particular embodiments, the invention can further comprise one or more of the following features, taken alone or according to all technically possible combinations.

In particular embodiments, the control unit of the planning device is further configured to segment an estimated ablation region represented on the simulated image.

In particular embodiments, the control unit of the planning device is further configured to associate, with each voxel of the estimated ablation region represented on the simulated image, a value called "X-ray density value" representative of an X-ray density of a tissue corresponding to said voxel.

In particular embodiments, the control unit is configured to segment the estimated ablation region such that each voxel of said estimated ablation region is associated with an X-ray density value above a predetermined threshold.

In particular embodiments, the control unit is configured to check that, for each point of the outline of the estimated ablation region, a gradient of the X-ray density values at that point in a direction normal to said outline is above a predetermined threshold.

In particular embodiments, the control unit is further configured to segment, on the preoperative image, a region to be treated corresponding to the tissue that the surgical procedure aims to ablate, and to compare the estimated ablation region represented on the simulated image with the region to be treated.

In particular embodiments, the control unit is further configured to check a validity condition which is satisfied if the outline of the estimated ablation region completely encompasses the outline of the region to be treated, and if, for each point of the outline of the estimated ablation region, the minimum distance between this point and the outline of the region to be treated lies within a predetermined range of values.

In particular embodiments, the control unit is further configured to determine one or more new sets of planning parameters for which the validity condition is satisfied, and to identify, from among these new sets of planning parameters, an optimal set of planning parameters for which the estimated ablation region exhibits minimal dimensions.

DESCRIPTION OF THE FIGURES

The invention will be better understood on reading the following description, given as a nonlimiting example, and with reference to FIGS. 1 to 10 which represent.

In these figures, references that are identical from one figure to another designate identical or similar elements. For reasons of clarity, the elements represented are not necessarily to the same scale, unless stipulated otherwise.

DETAILED DESCRIPTION OF AN
EMBODIMENT OF THE INVENTION

Figure 1:
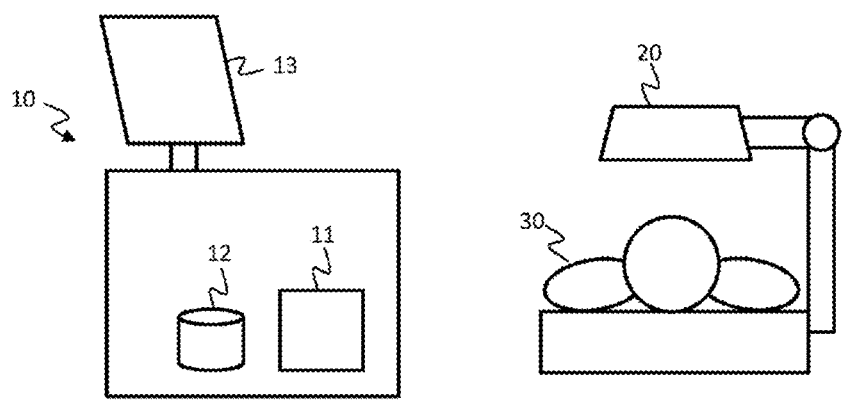
FIG. 1 a schematic representation of a device for planning a surgical procedure according to the invention, FIG. 2 a schematic representation of a preoperative image of an anatomical area of interest of a patient comprising a tissue to be ablated, FIG. 3 a schematic representation of a simulated image generated by the planning device on which an estimated ablation region has been segmented, FIG. 4 a schematic representation of a postoperative image of an anatomical area of interest of a patient on which an ablation region has been segmented following a surgical procedure that has ablated a tissue of said anatomical area of interest, FIG. 5 a schematic representation of the main steps of a method for planning a procedure aiming to ablate a tissue in an anatomical area of interest of a patient, FIG. 6 a schematic representation of a preoperative image of an anatomical area of interest of a patient on which a region to be treated has been segmented, FIG. 7 a schematic representation of a particular implementation of the planning method according to the invention, FIG. 8 a schematic representation of another particular implementation of the planning method according to the invention, FIG. 9 an illustration of the training of a neural network to implement a planning method according to the invention, FIG. 10 an illustration of the generation of a simulated image by a neural network to implement a planning method according to the invention.

FIG. 1 schematically represents a device 10 for planning a surgical procedure aiming to ablate a tissue in an anatomical area of interest of a patient 30.

Hereinafter in the description, the situation described, by way of nonlimiting example, is the case where the anatomical area of interest is the liver, and the tissue to be ablated is a tumor. It should however be noted that the invention is also applicable to other types of tissue that have to be ablated, such as cutaneous lesions, veins, nerves, cardiac tissues, esophagean tissues or even uterine fibromas. Also, the invention is applicable to other anatomical areas of interest such as, for example, a kidney, a lung, etc.

The planning device 10 comprises a control unit 11 comprising one or more processors and storage means 12 (magnetic hard disk, electronic memory, optical disk, etc.) in which is stored a computer program product, in the form of a set of program code instructions to be executed to implement at least a part of the steps of a surgical procedure planning method. Alternatively or additionally, the control unit comprises one or more programmable logic circuits (FGPA, PLD, etc.), and/or one or more custom integrated circuits (ASIC), and/or a set of discrete electronic components, etc., suitable for implementing said steps of the planning method.

In other words, the control unit 11 corresponds to means of the planning device 20 which are configured by software (specific computer program product) and/or hardware (FPGA, PLD, ASIC, discrete electronic components, etc.) to implement the steps of the planning method.

The planning device 10 can also comprise a graphical interface 13 allowing a user to supply the device 10 with the planning parameters and/or display an image or data generated by the device 10. In the example considered and illustrated in FIG. 1, the graphical interface 13 corresponds to a touch screen. The graphical interface could however also be produced using other devices such as a keyboard, a mouse, a screen, etc.

The planning device 10 uses as input data a set of planning parameters and a preoperative image of the anatomical area of interest of the patient 30. The planning device 10 implements a machine learning algorithm, to generate, from these input data, a simulated image on which an estimated ablation region is represented. Hereinafter in the description, it is considered by way of example and in a nonlimiting manner that the machine learning algorithm used is a neural network.

The planning parameters indicate for example a type of pathology to be treated (for example a hepatocellular carcinoma or metastases), a type of treatment for the ablation (radiofrequencies, microwaves, laser, electroporation, cryotherapy, etc.), a type of medical instrument to perform the treatment, a position and an orientation of the medical instrument at the time of treatment, treatment parameters (duration, power, etc.). The planning parameters are indicated on the graphical interface 13 by the practitioner who prepares the surgical procedure.

The preoperative image is obtained by a medical imaging device 20, for example by computerized tomography, by magnetic resonance, by ultrasound, by three-dimensional rotating angiography, by positon emission tomography, etc. The tissue to be ablated and the anatomical area of interest are visible on the preoperative image. The medical imaging device 20 can be a device distinct from the planning device 10. There is however nothing to prevent the planning device 20 and the medical imaging device 20 together forming one and the same physical entity. In the case where the planning device 20 and the medical imaging device 20 are distinct, the preoperative image can be transmitted to the planning device 10. For example, the preoperative image is digitized then transmitted to the planning device 10 by wireless communication means. According to another example, the digitized preoperative image can be supplied to the planning device 10 by a USB (Universal Serial Bus) type peripheral device.

The neural network is previously trained with learning elements each corresponding respectively to a similar tissue ablation surgical procedure in an anatomical area of interest performed previously for another patient. Each learning element comprises a preoperative image of the anatomical area of interest of said other patient, planning parameters used for said surgical procedure on that other patient, and a postoperative image of the anatomical area of interest of that other patient after the surgical procedure. In other words, the neural network is trained by "learning" what is the ablation region actually obtained on a postoperative image for a particular preoperative image and with particular planning parameters.

It should be noted that there is nothing to prevent a learning element of the neural network from corresponding to a past surgical procedure performed on the same patient as the patient for which the surgical procedure has been planned (the term "other patient" is therefore not to be taken in the strict sense).

Preferably, preoperative medical images of the learning elements of the neural network are of the same type as the preoperative medical image used as input datum to plan a surgical procedure.

A medical image used to form a learning element or used as input for the planning method can correspond to an image directly obtained by the medical imaging device 20. However, there is nothing to prevent such a medical image from corresponding to only a portion of an image obtained by the medical imaging device 20. In other words, it is for example possible to envisage reframing an image obtained by the medical imaging device 20 to provide the neural network with a medical image representing mainly the anatomical area of interest of the patient, or a portion of said anatomical area of interest in which the tissue to be treated is located.

Figure 2:
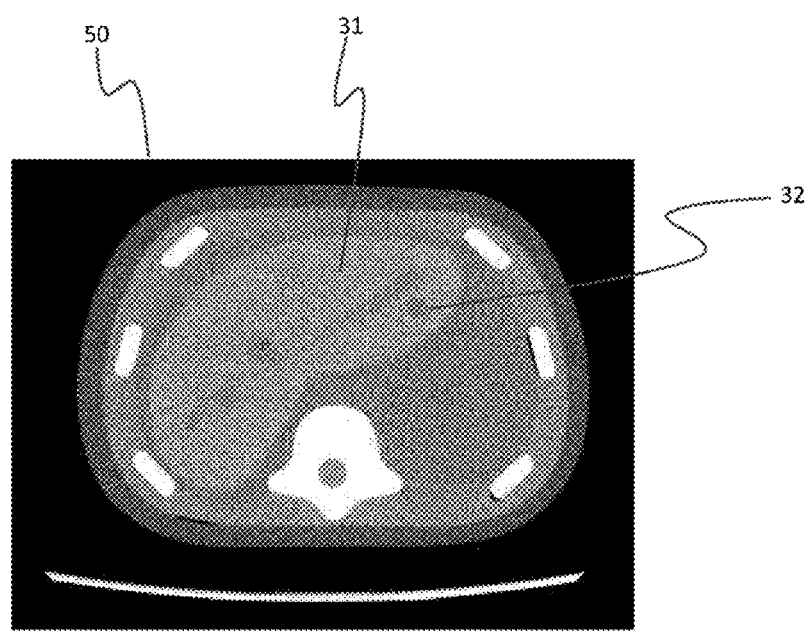

FIG. 2 schematically represents a preoperative image 50 of an anatomical area of interest 31 comprising a tissue 32 to be ablated. Such a preoperative image 50 corresponds, for example, to the preoperative image used as input datum to plan a surgical procedure. According to another example, such a preoperative image 50 can belong to a learning element used to train the neural network.

Figure 3:
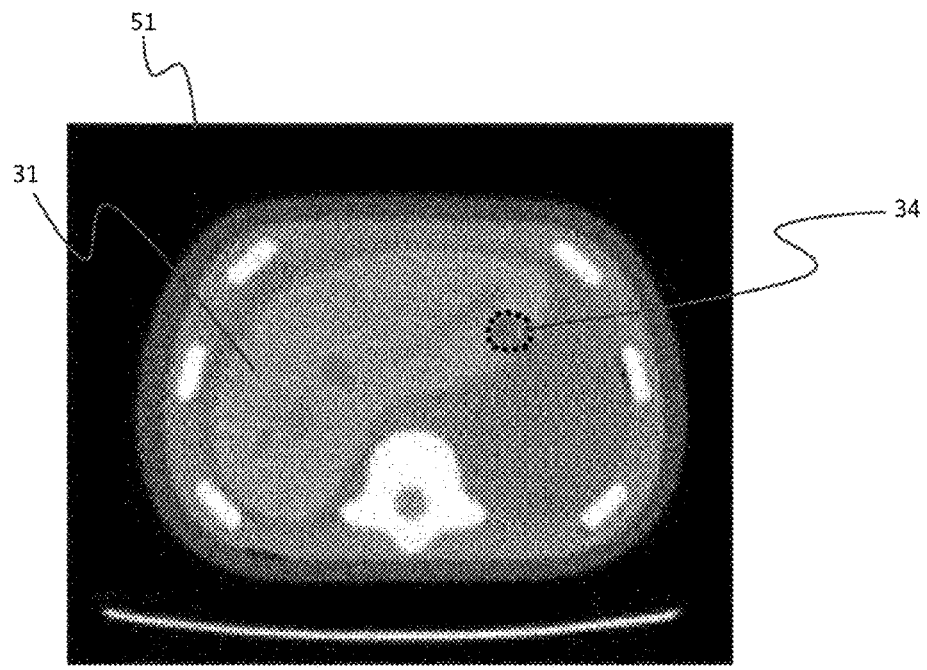

FIG. 3 schematically represents a simulated image 51 generated by the planning device 10 on which an estimated ablation region 34 has been segmented. In the example considered and illustrated in FIG. 3, the simulated image 51 was generated by the planning device 10 by taking as input datum the preoperative image 50 represented in FIG. 2.

Figure 4:
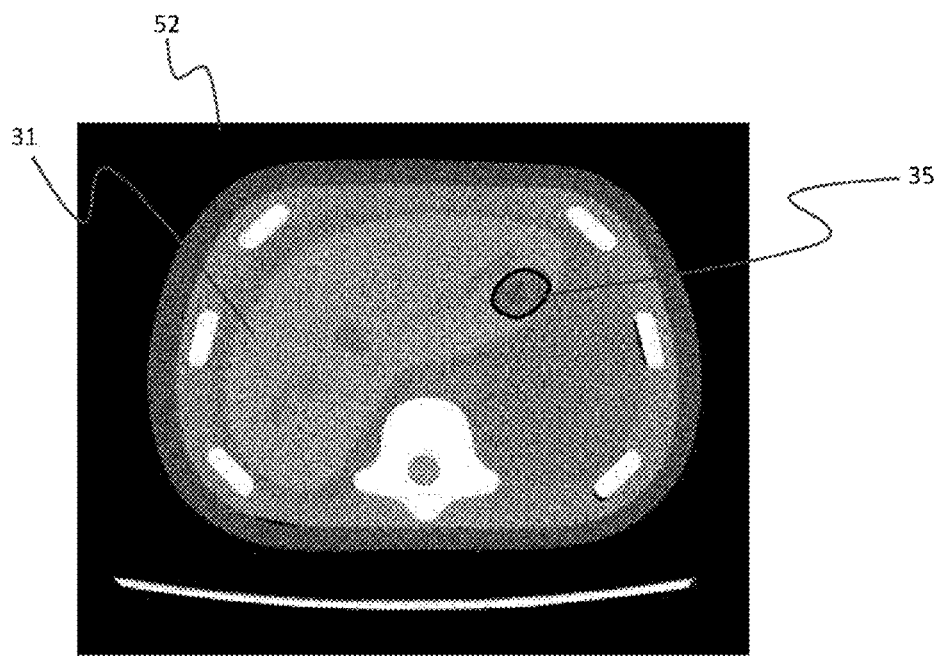

FIG. 4 schematically represents a postoperative image 52 of the anatomical area of interest 31 following a surgical procedure that has ablated the tissue 32. Such a postoperative image 52 can be used, in combination with the preoperative image 50 of FIG. 1, to form a learning element used to train the neural network. On the postoperative image 52 represented in FIG. 4, an ablation region 35 actually obtained following the surgical procedure has been segmented. This segmentation of the ablation region 35 actually obtained following the surgical procedure is not however essential for the postoperative image 52 to be able to be used to form a learning element of the neural network. It is moreover preferable not to segment the images used to form the learning elements of the neural network.

There are different methods for segmentation of an image. "Segmentation" is understood to mean an image processing operation whose aim is to define regions or outlines on an image according to predefined criteria. These methods are considered to be known to the person skilled in the art. By segmenting an ablation region that is estimated or actually obtained, it is possible to define dimensions of said ablation region.

Figure 5:
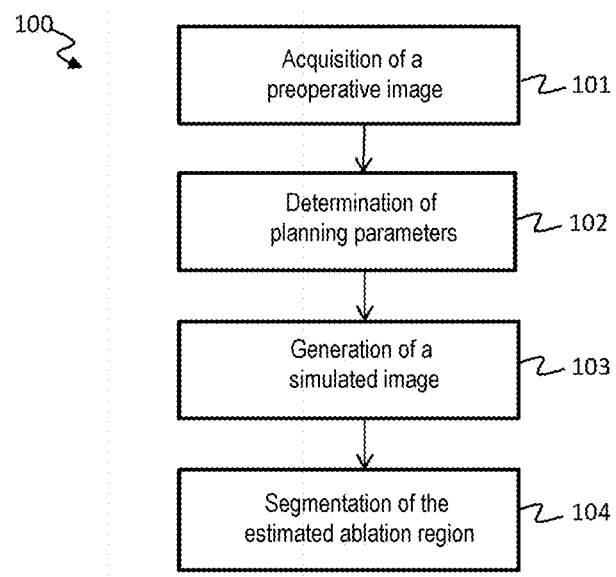

FIG. 5 schematically represents the main steps of a method 100 for planning a surgical procedure aiming to ablate a tissue 32 in an anatomical area of interest 31 of a patient 30.

The planning method 100 comprises the following steps:
an acquisition 101 of a preoperative image 50 of the anatomical area of interest 31,
a determination 102 of a set of planning parameters,
a generation 103 of a simulated image 51 by taking as input the preoperative image 50 and the planning parameters, and by using the neural network previously trained,
a segmentation 104 of an estimated ablation region 34 represented on the simulated image 51 generated by the neural network.

The step of acquisition 101 of a preoperative image is for example implemented by the practitioner using the imaging device 20 described with reference to FIG. 1.

The step of determination 102 of a set of planning parameters is for example implemented by the input, by the practitioner, via the graphical interface 13 of the planning device 10 described with reference to FIG. 1, of parameters relating to the surgical procedure to be performed (type of pathology, type of treatment, type of medical instrument used, position and orientation of the medical instrument, treatment parameters, etc.). There is however nothing to prevent some of these parameters from being determined automatically. For example, an optimal position and orientation of the medical instrument can be determined automatically by a learning algorithm.

The steps of generation 103 of the simulated image 51 and of segmentation 104 of the estimated ablation region 34 are for example implemented by the neural network implemented in the control unit 11 of the planning device 10.

The simulated image 51 generated allows the practitioner to observe the result that he or she is likely to obtain after the surgical procedure if he or she uses the planning parameters which have been provided as input data to the planning method 100.

The estimated ablation region 34 can have greater or lesser dimensions compared to a region to be treated corresponding to the tissue to be ablated.

It should be noted that the step of segmentation 104 of an estimated ablation region 34 represented on the simulated image 51 is optional because it is not essential to the invention. Notably, the ablation region can be identifiable by the practitioner on the simulated image 51 without a segmentation of said estimated ablation region 34 being performed.

Figure 6:
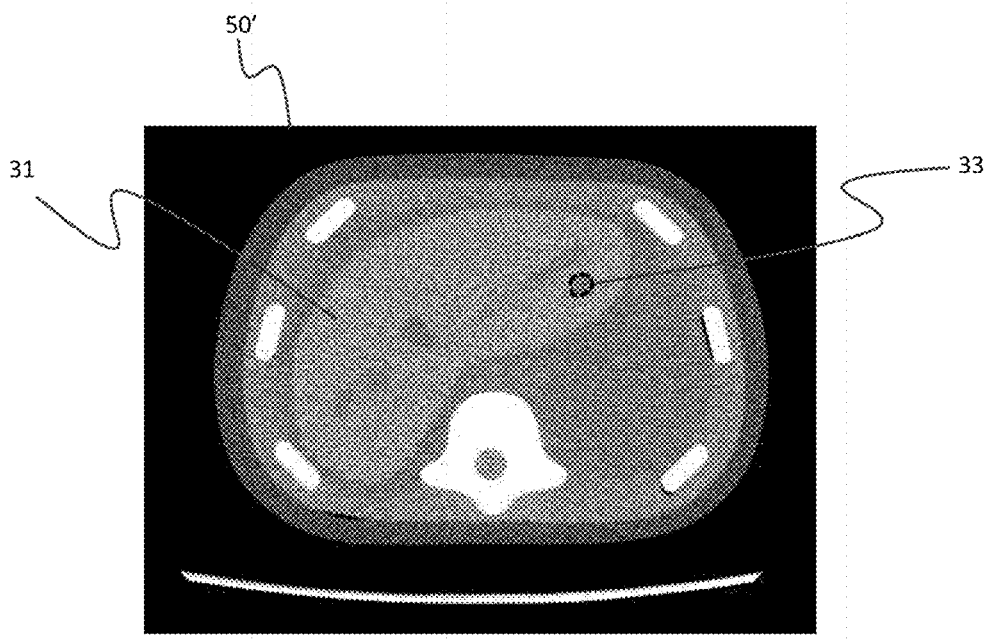

FIG. 6 schematically represents a preoperative image 50' corresponding to the preoperative image 50 of FIG. 2 on which the region to be treated 33 corresponding to the tissue 32 to be ablated is segmented. It is advantageous to compare the dimensions of the estimated ablation region 34 with the dimensions of the region to be treated 33. In fact, it is best here to check that the region to be treated is sufficiently covered by the treatment while minimizing the dimensions of the ablation region in order not to destroy the largest parts of healthy tissue which do not form part of the region to be treated.

Figure 7:
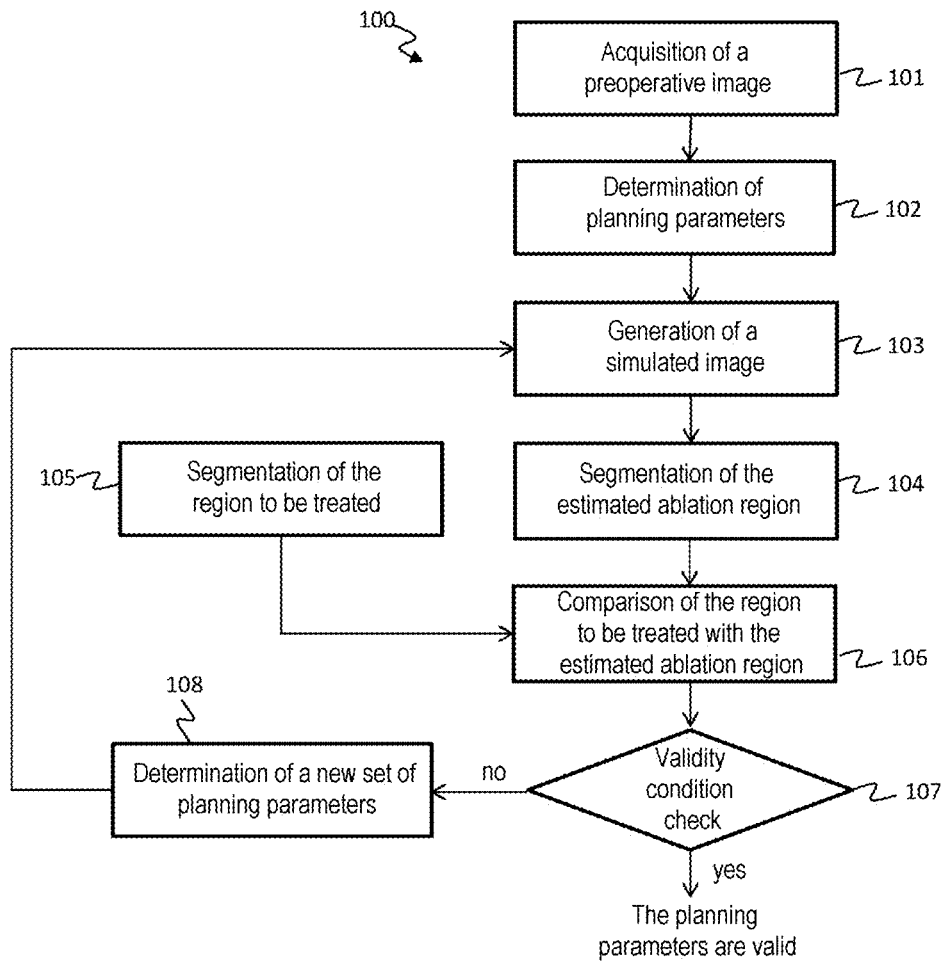

FIG. 7 schematically represents the main steps of a particular implementation of the planning method 100 according to the invention. In addition to the steps described previously with reference to FIG. 5, the particular implementation illustrated in FIG. 7 comprises the following steps:
a segmentation 105 on the preoperative image 50 of a region to be treated 33 corresponding to the tissue 32 that the surgical procedure aims to ablate,
a comparison 106 of the estimated ablation region 34 represented on the simulated image with the region to be treated 33,
a check 107 on a validity condition.

For example, the validity condition is borne out if the outline of the estimated ablation region 34 completely encompasses the outline of the region to be treated 33 and if, for each point of the outline of the estimated ablation region 34, the minimum distance between this point and the outline of the region to be treated 33 lies within a predetermined range of values. For example, the predetermined range of values corresponds to the values lying between 5 and 10 millimeters. Other validity conditions can however be envisaged and constitute only variants of the invention.

When the check 107 on the validity condition is negative, the practitioner may for example decide to modify the planning parameters and run another simulation.

According to another example, and as illustrated in FIG. 7, the method 100 can comprise a step of determination 108, automatically by the planning device 10, of a new set of planning parameters for which the estimated ablation region 34 satisfies the validity condition. The determination step 108 is for example performed by conventional methods of optimization and of exploration of the space of the planning data.

Figure 8:
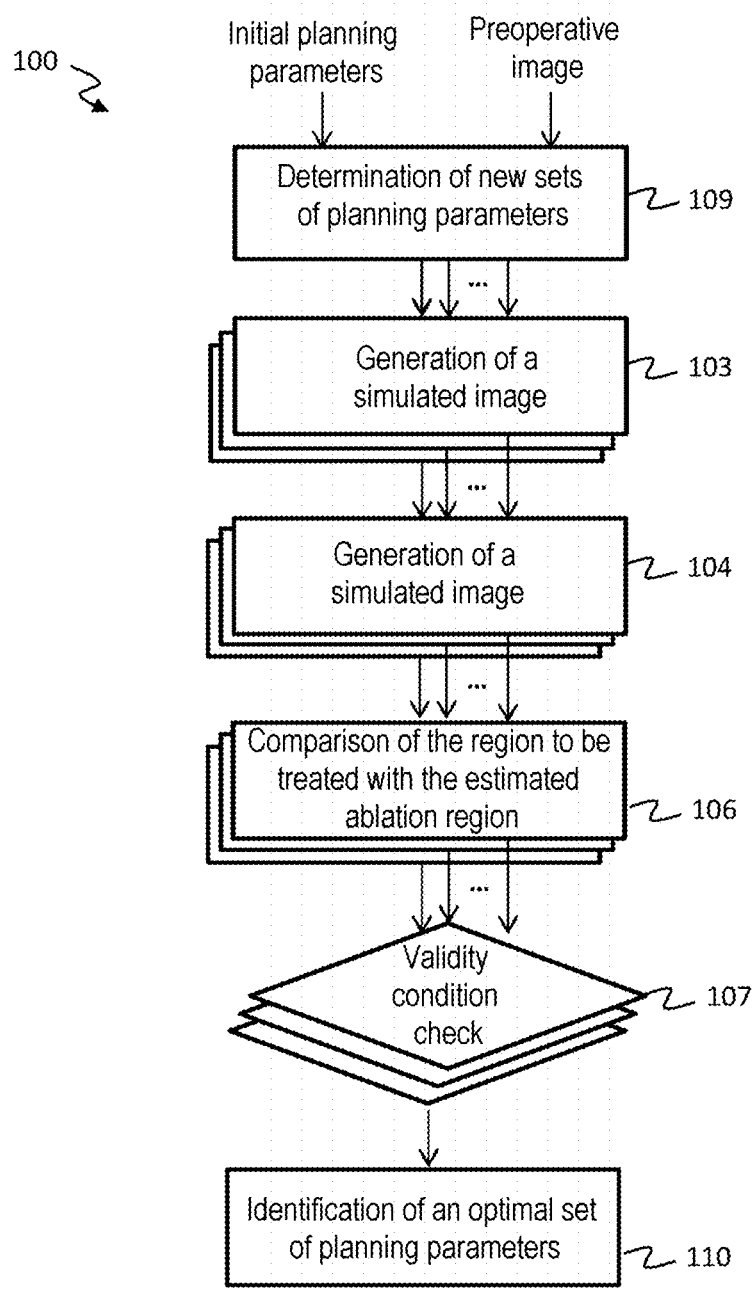

FIG. 8 represents yet another particular implementation of the planning method 100 according to the invention. In this particular implementation, the planning method 100 comprises a step of determination 109 of several new sets of planning parameters. As illustrated in FIG. 8, for each new set of planning parameters, the steps of generation 103 of a simulated image, of segmentation 104 of an estimated ablation region, of comparison 106 between the region to be treated and the estimated ablation region, and of checking 107 the validity condition, are performed. The method 100 next comprises a step of identification 110, from among the new sets of planning parameters which bear out the validity condition, of an optimal set of planning parameters. For example, the optimal set of planning parameters corresponds to the planning parameters for which the estimated ablation region 34 exhibits minimal dimensions while bearing out the validity condition. That thus makes it possible to minimize the quantity of healthy tissue ablated during the surgical procedure.

It should be noted that, in FIG. 8, the new sets of planning parameters are determined then validated in parallel. There is however nothing to prevent the new sets of planning parameters from being determined iteratively, one after the other. If necessary, a new set of planning parameters can be determined as a function of another new set of planning parameters previously determined, and/or as a function of the planning parameters initially chosen by the practitioner.

Different methods can be envisaged for determining and segmenting the estimated ablation region on the simulated image 51 generated by the neural network.

According to a first method, the estimated ablation region is represented by a binary image which is overlaid on the preoperative image 50 to form the generated image 51. In this case, each voxel of the binary image situated outside of the estimated ablation region is associated with a zero value, and each voxel situated inside the estimated ablation region is associated with a fixed non-zero value. A voxel for which the value is non-zero appears with a particular color on the binary image. A voxel for which the value is zero is, on the other hand, transparent and has no impact on the generated image when it is overlaid on the preoperative image. To recap, in the case where the images used are in two dimensions, the term voxel can be replaced by the term pixel.

According to a second method, the estimated ablation region is segmented on the simulated image 51 as a function of a tissue response of the anatomical area of interest 31 to the ablation procedure. To this end, a tissue response to the ablation procedure is determined by the neural network by associating, with each voxel of the estimated ablation region 34 represented on the simulated image 51, a value, called "X-ray density value", representative of an X-ray density of a tissue corresponding to said voxel.

The X-ray density is representative of the relative inability of electromagnetic radiations, for example X-rays generated by the medical imaging device 20, to pass through a tissue of the anatomical area of interest 31 of the patient (it should be noted that the aim of the X-rays emitted by the imaging device is not to ablate the tumor, and the "X-ray density value" discussed here is independent of the radiotherapy parameters). The ablation region represented on the simulated image 51 by the neural network corresponds generally to a necrosed region which, on the image, presents lower X-ray density values than a part of the anatomical area of interest of the patient which has not been ablated. The more a voxel of the ablation region is associated with a low X-ray density value, the more the part of the ablation region corresponding to said voxel has been destroyed. "Tissue response to the ablation procedure" is thus understood to mean a representation of the proportion with which each part of the tissue to be treated has been ablated. For example, the voxels of the ablation region for which the X-ray density value is above a predetermined first threshold correspond to the parts of the tissue to be treated that have been at least 50% destroyed. According to another example, the voxels of the ablation region for which the X-ray density value is below a predetermined second threshold correspond to the parts of the tissue to be treated that have been more than 90% destroyed. It is thus possible to map, from the simulated image, the estimated response of the tissue to the treatment.

The segmentation 104 of the estimated ablation region 34 can then for example be performed such that each voxel of said estimated ablation region is associated with an X-ray density value above a predetermined threshold. That thus makes it possible to ensure that any tissue situated within the outline of the segmentation of the ablation region has been destroyed beyond a certain desired proportion (for example more than 90%).

The X-ray density value associated with a voxel is for example defined on the basis of the Hounsfield scale.

In particular implementations, the planning method 100 comprises a step of checking that, for each point of the outline of the estimated ablation region 34, a gradient of the X-ray density values at this point in a direction normal to said outline is above a predetermined threshold. The gradient represents the variability of the X-ray density values at the point considered in a direction normal to the outline ("direction normal to the outline" is understood to mean the direction at right angles to a tangent to the outline passing through the point considered). Such provisions notably make it possible to check whether the outline of the ablation region is sharp. The outline of the ablation region marks the limit between the treated region and the untreated tissue. The sharpness of this outline is representative of the quality of the ablation. At a point of the outline of the estimated ablation region 34, the higher the gradient, the greater the variation of the X-ray density values between the ablation region and the unablated healthy tissue.

It is sometimes possible to observe, on a medical image representing an ablation region, a white form in the form of a ring of small thickness which surrounds the ablation region. The presence or not of this ring can be representative of the quality of the ablation. By calculating a gradient at each point of the estimated ablation region 34 and comparing this gradient with a predetermined threshold, it is possible to increase the reliability of the estimation of the quality of the ablation (for example, if the gradient is above a threshold at all points of the outline, the ablation can be considered to be of good quality even if the white ring is not directly visible on the medical image to the naked eye).

In a preferred embodiment, the neural network is a convolutional neural network. Convolutional neural networks are particularly well suited to image recognition. Such a neural network 40 is represented schematically in FIGS. 9 and 10. The neural network 40 comprises several layers of artificial neurons. There are processing neurons, which process a limited portion of an image through a convolution function, and output pooling neurons. The set of outputs of a processing layer makes it possible to reconstruct an intermediate image which will serve as basis for the next layer. The neural network 40 also comprises an entirely connected layer 41 which has connections to all the outputs of the preceding layers, and a prediction layer 42 at the output of which the simulated image 51 is generated. It is the prediction layer 42 which makes it possible, in particular, to assign an X-ray density value to each voxel of the simulated image 51.

Figure 9:
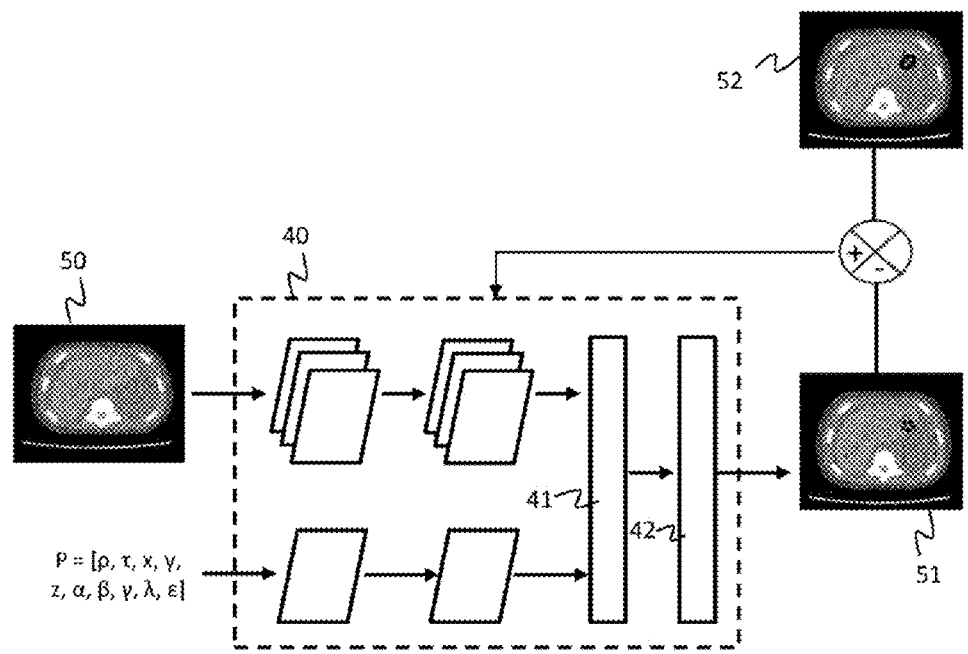

FIG. 9 schematically illustrates a training phase (or learning phase) of the neural network 40. The neural network is trained with learning elements each corresponding respectively to a tissue ablation surgical procedure in an anatomical area of interest for a patient. Each learning element comprises a preoperative image 50 of the anatomical area of interest of the patient, planning parameters P used for the surgical procedure on that patient, and a postoperative image 52 of the anatomical area of interest of that patient after the surgical procedure.

Among the possible planning parameters P, the following can be cited:

- The type of pathology ρ: for example, the pathology can be a hepatocellular carcinoma or metastases. A particular type of pathology can be associated with a particular value for the parameter ρ.
- The treatment type τ: the ablation of the tissue can for example be performed by microwaves, radiofrequencies, cryotherapy, electroporation, laser, focused ultrasound, etc. A particular type of treatment can be associated with a particular value for the parameter τ.
- The coordinates x, y, z of the position of the medical instrument (for example the position of the point of a needle): they can be expressed by a predetermined reference frame (for example a reference frame of the preoperative image).
- The angles α, β, γ representing the orientation of the medical instrument (for example the orientation of the needle) in the reference frame considered.
- The type of medical instrument λ: a particular type of medical instrument (model, manufacturer, etc.) can be associated with a particular value for the parameter λ.
- The treatment parameters ε: based on the type of treatment, different treatment parameters can be defined, for example a treatment power or duration.

When several treatments are performed simultaneously with several medical instruments, the planning parameters P can be written in the form $P=[\rho_1, \tau_1, x_1, y_1, z_1, \alpha_1, \beta_1, \gamma_1, \lambda_1, \varepsilon_1, \ldots, \rho_N, \tau_N, x_N, y_N, z_N, \alpha_N, \beta_N, \gamma_N, \lambda_N, \varepsilon_N]$, in which N represents the number of treatments.

During the training, for each learning element, the neural network 40 determines, for each neuron, a set of weights and of biases that make it possible to obtain a simulated image 51 that is as similar as possible to the postoperative image 52 based on the preoperative image 50 coupled with the planning parameters P.

The estimated ablation region 34 on the simulated image 51 is compared to the real ablation region of the postoperative image 52 by the neural network 40 by using a loss function which is then used to calculate an overall cost function. An optimization process then searches for the weight and bias parameters which minimize this overall cost function. The optimization process can be performed iteratively.

Preferably, the learning elements correspond to past procedures which cover all the pathologies and all the treatments envisaged.

Figure 10:
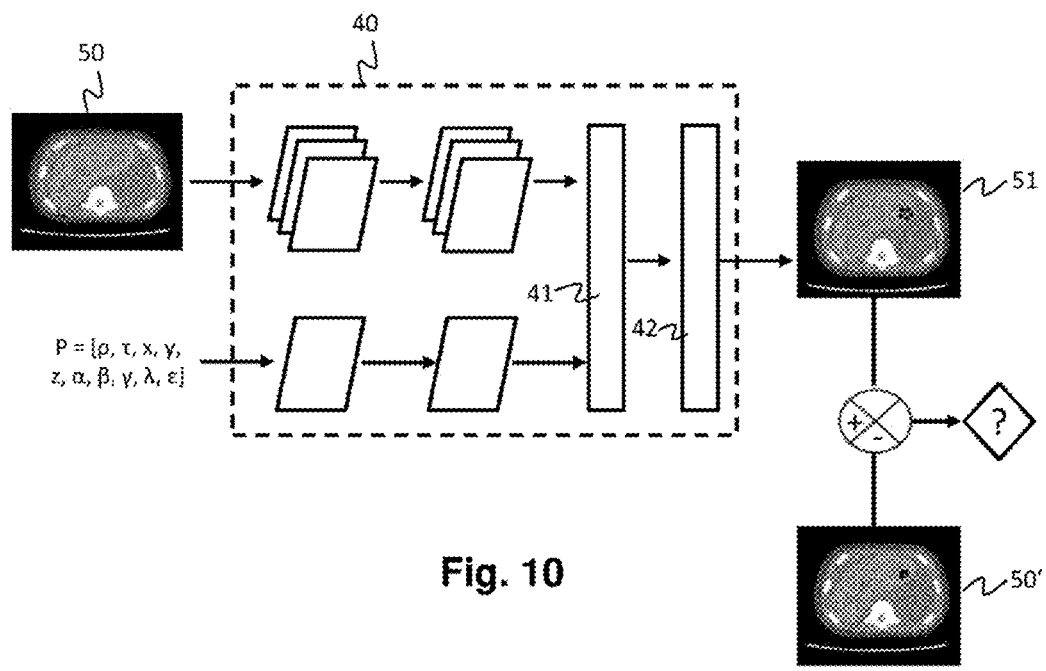

FIG. 10 schematically illustrates a planning phase by the neural network 40 for a tissue ablation procedure in an anatomical area of interest of a patient. The neural network 40 receives as input the preoperative image 50 of said anatomical area of interest of the patient and planning parameters P envisaged by the practitioner. The neural network selects the characteristics of the preoperative image 50 describing the tissue of interest and its vicinity which are likely to modify the ablation region. A simulated image 51 representing an estimated ablation region is then generated by the neural network. It is then possible to compare the estimated ablation region represented on the simulated image 51 with the region to be treated represented on the preoperative image 50'. If the estimated ablation region is not satisfactory (for example, if it does not cover all the region to be treated or else if it covers it with excessive margins), new planning parameters can be defined, either by the practitioner or automatically by the planning device 10. A set of planning parameters making it possible to obtain a satisfactory estimated ablation region can then be determined. These parameters will then be used subsequently, on the day of the surgical procedure. The planning parameters can for example be used to configure a medical robot which assists the practitioner during the medical procedure. Some parameters, notably those linked to the position and the orientation of the medical instrument, will if necessary be able to be adjusted using a realignment between the preoperative image 50 used to plan the surgical procedure and an intraoperative image obtained during the surgical procedure.

It should be noted that the planning method 100 according to the invention does not include any surgical step on the patient. It is in fact a planning method 100, and the duly planned surgical procedure takes place subsequent to the planning method 100, possibly several days after. Also, the training phase of the neural network is performed after surgical procedures performed on other patients. These surgical procedures should not be considered to form part of the training phase of the neural network.

It should also be noted that the neural network 40 can take as input an image on which a tissue already partially ablated is visible, in order to define an additional treatment that needs to be applied to complete the ablation. Thus, for a procedure in which several treatments have to be performed in succession, it is then possible to iterate the method according to the invention several times to each time refine the treatments initially planned.

The description above clearly illustrates that, through its various features and the advantages thereof, the present invention achieves the objectives set for it. In particular, all of the information contained in the medical image of the anatomical area of interest of the patient is taken into account to make the prediction of the ablation region. The prediction of the ablation region is therefore entirely specific to a given patient. Furthermore, the neural network is capable of learning what the impact of using several medical instruments in a procedure is in order to estimate, with greater accuracy, what the ablation region obtained is in such a case. Furthermore, the planning method according to the invention requires no in vivo measurement of the patient, which makes it possible to perform the planning upstream of the surgical procedure in order to offer the practitioner more time to prepare the procedure. The estimation of the tissue response to the treatment makes it possible to even more accurately predict the result of the ablation.

The invention claimed is:

1. A method for planning a surgical procedure aiming to ablate a tissue in an anatomical area of interest of a patient, said method comprising:
    acquiring a preoperative image of said anatomical area of interest, and
    determining a set of planning parameters (P),
    generating a simulated image in which an estimated ablation region is represented, said simulated image being generated on a basis of said preoperative image, of said planning parameters (P), and of a neural network, said neural network having been previously trained with a plurality of learning elements, each learning element corresponding respectively to a similar tissue ablation surgical procedure in an anatomical area of interest for another patient, each learning element comprising a preoperative image of the anatomical area of interest of said other patient, planning parameters (P) used for said surgical procedure on that other patient, and a postoperative image of the anatomical area of interest of that other patient after the surgical procedure, said simulated image making it possible to observe a result likely to be obtained after the surgical procedure, segmenting the estimated ablation region represented on the simulated image, segmenting the preoperative image of a region to be treated corresponding to the tissue that the surgical procedure aims to ablate, comparing the estimated ablation region represented on the simulated image with the region to be treated, determining a tissue response to the ablation procedure by associating, with each voxel of the estimated ablation region represented on the simulated image, an X-ray density value, representative of an X-ray density of a tissue corresponding to said voxel, and checking that, for at least one point of the estimated ablation region, a gradient of X-ray density value at the at least one point is above a predetermined threshold.

2. The method of claim 1, wherein the segmenting of the estimated ablation region is performed such that each voxel of said estimated ablation region is associated with the X-ray density value above the predetermined threshold.

3. The method of claim 1, further comprising a check that, for each point of an outline of the estimated ablation region, a gradient of the X-ray density value at this point in a direction normal to said outline is above the predetermined threshold.

4. The method of claim 1, further comprising a check on a validity condition which is satisfied if an outline of the estimated ablation region completely encompasses the outline of the region to be treated, and if, for each point of the outline of the estimated ablation region, a minimum distance between this point and the outline of the region to be treated lies within a predetermined range of values.

5. The method of claim 4, wherein, when the check on the validity condition is negative, the method comprises a determination of a new set of planning parameters for which the estimated ablation region satisfies the validity condition.

6. The method of claim 4, further comprising determining several new sets of planning parameters for which the validity condition is satisfied, and a step of identification, from among the new sets of planning parameters, of an optimal set of planning parameters for which the estimated ablation region exhibits minimum dimensions.

7. The method of claim 1, wherein the anatomical area of interest is the liver.

8. The method of claim 1, wherein the tissue to be ablated is a tumor.

9. The method of claim 1, wherein the planning parameters (P) comprise one or more elements from among the following elements:
 a type of pathology,
 a type of treatment,
 a type of medical instrument to be used for the treatment,
 a position and/or an orientation of the medical instrument to be used for the treatment,
 treatment parameters specific to the medical instrument, and/or
 a number of treatments to be performed during the surgical procedure.

10. A non-transitory computer program product, comprising a set of program code instructions which, when they are executed by one or more processors, configure the processor or processors to generate, using a neural network, a simulated image on which there is represented an estimated ablation region, from, a preoperative image of an anatomical area of interest of a patient comprising a tissue to be ablated, and, planning parameters (P), said neural network being adapted to be trained previously with a plurality of learning elements, each learning element corresponding respectively to a similar tissue ablation surgical procedure in an anatomical area of interest for another patient, each learning element comprising a preoperative image of the anatomical area of interest of said other patient, planning parameters (P) used for said surgical procedure on that other patient, and a postoperative image of the anatomical area of interest of that other patient after the surgical procedure, segment an estimated ablation region represented on the simulated image, segment, on the preoperative image, a region to be treated corresponding to the tissue that the surgical procedure aims to ablate, compare the estimated ablation region represented on the simulated image with the region to be treated, associate, with each voxel of the estimated ablation region represented on the simulated image, an X-ray density value representative of an X-ray density of a tissue corresponding to said voxel, and a check that, for at least one point of the estimated ablation region, a gradient of X-ray density value at the at least one point is above a predetermined threshold.

11. A device for planning a surgical procedure aiming to ablate a tissue in an anatomical area of interest of a patient, wherein said device comprises a control unit configured to:
 generate a simulated image based on a preoperative image of said anatomical area of interest, a set of planning parameters (P), and a neural network, said neural network being adapted to be previously trained with a plurality of learning elements, each learning element being associated respectively with a similar tissue ablation surgical procedure in an anatomical area of interest for another patient, each learning element comprising a preoperative image of the anatomical area of interest of said other patient, planning parameters (P) used for said surgical procedure on that other patient, and a postoperative image of the anatomical area of interest of that other patient after a surgical procedure,
 segment, an estimated ablation region represented on the simulated image,
 segment, on the preoperative image, a region to be treated corresponding to the tissue that the surgical procedure aims to ablate,
 compare the estimated ablation region represented on the simulated image with the region to be treated,
 wherein said control unit is further configured to associate, with each voxel of the estimated ablation region represented on the simulated image, an X-ray density value representative of an X-ray density of a tissue corresponding to said voxel, and
 check that, for at least one point of the estimated ablation region, a gradient of X-ray density value at the at least one point is above a predetermined threshold.

12. The device of claim 11, wherein said control unit is configured to segment the estimated ablation region such that each voxel of said estimated ablation region is associated with the X-ray density value above the predetermined threshold.

13. The device of claim 11, wherein said control unit is configured to check that, for each point of an outline of the estimated ablation region, a gradient of the X-ray density value at that point in a direction normal to said outline is above the predetermined threshold.

14. The device of claim 11, wherein said control unit is further configured to check a validity condition which is satisfied if an outline of the estimated ablation region completely encompasses the outline of the region to be treated, and if, for each point of the outline of the estimated ablation region, a minimum distance between that point and the outline of the region to be treated lies within a predetermined range of values.

15. The device of claim 14, wherein said control unit is further configured to determine one or more new sets of planning parameters for which the validity condition is satisfied, and to identify, from among these new sets of planning parameters, an optimal set of planning parameters for which the estimated ablation region exhibits minimum dimensions.

* * * * *